US008158838B2

(12) United States Patent
Koo et al.

(10) Patent No.: US 8,158,838 B2
(45) Date of Patent: Apr. 17, 2012

(54) DIADEHYDE COMPOUND, PREPARATION METHOD THEREOF, AND SYNTHETIC METHOD OF CAROTENOIDS USING THE SAME

(75) Inventors: Sang Ho Koo, Seoul (KR); Eun Ho Choi, Kyunggi-do (KR); Joo-Won Suh, Gyeonggi-do (KR)

(73) Assignee: Myongji University Industry and Academia Cooperation, Gyeonggi-do (KR)

( * ) Notice: Subject to any disclaimer, the term of this patent is extended or adjusted under 35 U.S.C. 154(b) by 0 days.

(21) Appl. No.: 13/047,524

(22) Filed: Mar. 14, 2011

(65) Prior Publication Data

US 2011/0166400 A1    Jul. 7, 2011

Related U.S. Application Data

(60) Division of application No. 12/308,028, filed on Dec. 5, 2008, now Pat. No. 7,928,266, which is a continuation of application No. PCT/KR2007/002511, filed on May 23, 2007.

(30) Foreign Application Priority Data

Jun. 5, 2006 (KR) ........................ 10-2006-0050248

(51) Int. Cl.
   *C07C 1/32* (2006.01)
(52) U.S. Cl. ...................................... 585/327
(58) Field of Classification Search ........................ None
   See application file for complete search history.

(56) References Cited

U.S. PATENT DOCUMENTS 5,185,468 A     2/1993   Mori et al.
6,331,652 B1 *  12/2001  Konya et al. ................. 568/9

FOREIGN PATENT DOCUMENTS

| DE | 954247 | 12/1956 |
| WO | 03037854 A1 | 5/2003 |
| WO | 2006038764 A1 | 4/2006 |

OTHER PUBLICATIONS

Ji, M., et al., Allylic Sulfones Containing Triene Moieties as Key Synthons for Carotenoid Synthesis, Helv. Chim. Acta 2003, 86, 2620-2628.
Guha, S., et al., Sulfone Coupling and Double-Elimination Strategy for Carotenoid Synthesis, J. Org. Chem. 2005, 70, 9662-9665.
Choi, H., et al., Diallylic Sulfides as Key Structures for Carotenoid Syntheses, J. Org. Chem. 1999, 64, 8051-8053.
Choi, S., et al., Efficient Syntheses of the Keto-carotenoids Canthaxanthin, Astaxanthin, and Astacene, J. Org. Chem. 2005, 70, 3328-3331.
Barrero et al., {Reductive Coupling of Terpenic Allylic Halides Ctalyzed by Cp2TiCl: A Short and Efficient Asymmetric Synthesis of Onocerane Triterpenes, Orgainic Letters (2005), 7(12), 2301-2304}.
Otera, J., et al., Stereocontrolled Synthesis of Vitamin A Through a Double Elimination Reaction. A Novel Convergent C10 + C10 Route, J. Org. Chem. 1986, 51, 3834-3838, Publication date (web) May 1, 2002, downloaded from http://pubs.acs.org on Apr. 10, 2009.
Umbreit, M.A., et al., Allylic Oxidation of Olefins by Catalytic and Stoichiometric Seleium Dioxide With Tert-butyl Hydroperoxide, J. Am Chen Soc. 1977, 99, 5526-5528. Publication Date (web): May 1, 2002, downloaded from http://pubs.acs.org on Apr. 10, 2009.
Official Search Report of the Patent Cooperation Treaty in counterpart foreign Application No. PCT/KR2007/002511, filed May 23, 2007.

\* cited by examiner

Primary Examiner — Kamal Saeed
(74) Attorney, Agent, or Firm — Kinney & Lange, P.A.

(57) ABSTRACT

The novel C dialdehyde compound which can be efficiently utilized in the synthesis of carotenoid compounds based on the sulfone chemistry, the preparation method of the same, and the expeditious and practical synthetic processes for lycopene and β-carotene by the use of the above novel compound are disclosed. The syntheses of lycopene and β-carotene are characterized by the processes of the coupling reaction between two equivalents of geranyl sulfone or cyclic geranyl sulfone and the above C dialdehyde, the functional group transformation reactions of the diol in the resulting C 40 coupling products to X's (either halogens or ethers), and the double elimination reactions of the functional groups of the benzenesulfonyl and X to produce the fully conjugated polyene chain of the carotenoids.

2 Claims, No Drawings

DIALDEHYDE COMPOUND, PREPARATION METHOD THEREOF, AND SYNTHETIC METHOD OF CAROTENOIDS USING THE SAME

CROSS-REFERENCE TO RELATED APPLICATION(S)

This application is a division of U.S. application Ser. No. 12/308,028 filed Dec. 5, 2008 for "Dialdehyde Compound, Preparation Method Thereof, and Synthetic Method of Carotenoids Using the Same" by S. Koo, E. Choi and J. Soo, which is the national phase of PCT Application No. PCT/KR2007/002511 filed May 23, 2007.

INCORPORATION BY REFERENCE

U.S. application Ser. No. 12/308,028 is hereby incorporated by reference in its entirety.

TECHNICAL FIELD

The present invention relates to a novel $C_{20}$ dialdehyde, synthetic method thereof, and synthetic method of the carotenoid compounds using the same. More specifically, it relates to 8-arenesulfonyl-2,6,11,15-tetramethyl-2,6,10,14-hexadecatetraenedial, which can be efficiently utilized in the synthesis of carotenoid natural products containing the conjugated polyene chain, a process for preparing the same, and a process for the expeditious and practical synthesis of lycopene and β-carotene by using the above novel $C_{20}$ compound.

BACKGROUND ART

The carotenoid compounds, represented by lycopene, β-carotene, canthaxanthin, and astaxanthin, belong to the family of isoprenoid natural products, and have been industrially utilized as non-hazardous dyes for foodstuffs and key ingredients of cosmetics due to the characteristic red colors. The carotenoids are also widely utilized as functional food-additives and nutraceutical agents because of their anti-oxidizing efficiencies and prophylaxis effects on cancers of prostate, breast, lung, and etc.

The representative synthetic methods of carotenoids utilize the Wittig reaction, which have been the commercial process of BASF (Scheme 1). The reaction of two equivalents of the acyclic $C_{15}$ phosphonium salt (A) and the $C_{10}$ dialdehyde (C) produced lycopene of the Chemical Formula 1 (Ernst, H. *Pure Appl. Chem.* 2002, 74, 2213-2226). The Wittig reaction of two equivalents of the cyclic $C_{15}$ phosphonium salt (B) and the $C_{10}$ dialdehyde (C) provided β-carotene of the Chemical Formula 2 (Wittig, G.; Pommer, H. German Patent 954,247, 1956). These BASF processes are efficient in retro-synthetic point of view, but still have the problems related with the Wittig reaction: (1) the difficulty in separation of the by-product, phosphine oxide ($Ph_3P=O$), (2) the formation of the biologically less active Z-configuration in the carbon-carbon double bonds. Non-trivial synthetic procedures for the above $C_{15}$ phosphonium salts (A) and (B), and the $C_{10}$ dialdehyde (C), all in E-configuration, have also demanded more efficient and practical synthetic pathway to the carotenoid compounds.

Scheme 1

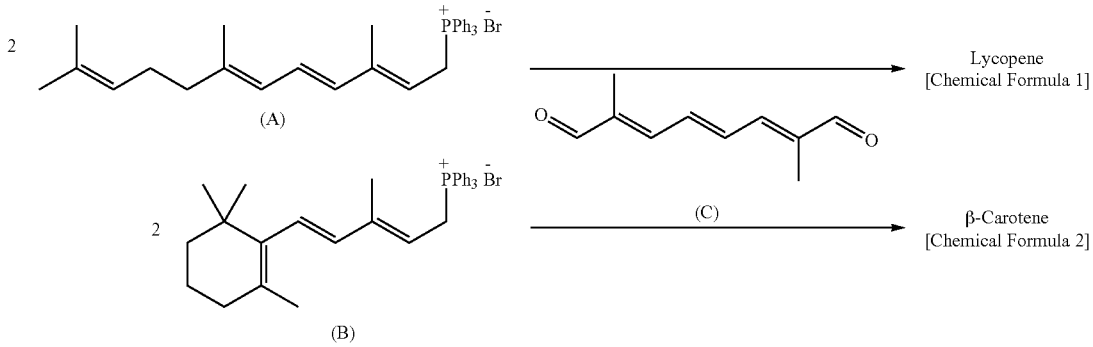

To overcome the afore-mentioned problems, we recently developed practical synthetic methods of the carotenoid compounds as illustrated in Scheme 2. The coupling reaction of two equivalents of the $C_{15}$ alkylic sulfone compound (D) with the $C_{10}$ bis(chloroallylic) sulfide compound (F) or the $C_{10}$ bis(chloroallylic) sulfone compound (G), followed by the Ramberg-Backlund reaction and then dehydrosulfonylation reaction produced lycopene of the Chemical Formula 1 (Ji, M.; Choi, H.; Jeong, Y. C.; Jin, J.; Baik, W.; Lee, S.; Kim, J. S.; Park, M.; Koo, S. *Helv. Chim. Acta* 2003, 86, 2620-2628). Two equivalents of the $C_{15}$ alkylic sulfone compound (D) were also reacted with the $C_{10}$ dialdehyde compound (H) to give the $C_{40}$ coupling product, in which the resulting diols were halogenated or converted to various diether functional groups before the double elimination reactions to provide lycopene of the Chemical Formula 1 (Guha, S. K.; Koo, S. *J. Org. Chem.* 2005, 70, 9662-9665).

Scheme 2

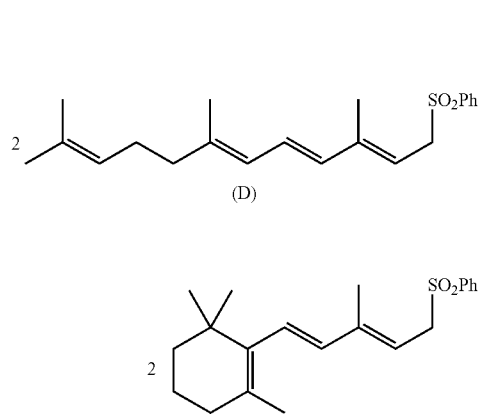

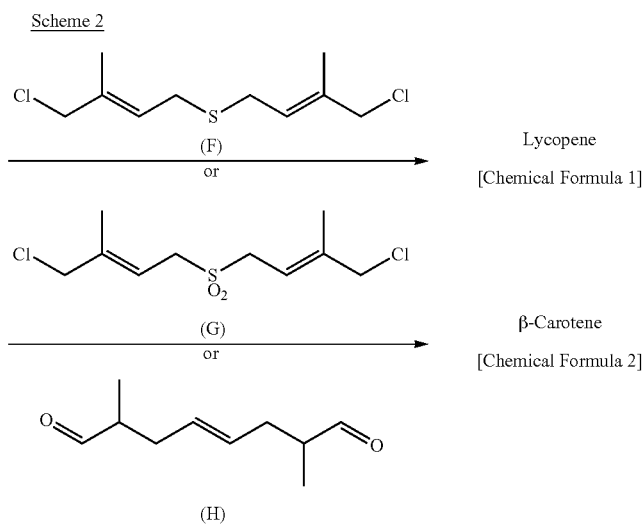

On the other hand, the applications of the above procedures to two equivalents of the cyclic $C_{15}$ alkylic sulfone compound (E) and each of the $C_{10}$ unit: bis(chloroallylic) sulfide compound (F), the $C_{10}$ bis(chloroallylic) sulfone compound (G) or the $C_{10}$ dialdehyde compound (H) nicely produced β-carotene of the Chemical Formula 2 (Choi, H.; Ji, M.; Park, M.; Yun, I.-K.; Oh, S.-S.; Baik, W.; Koo, S. *J. Org. Chem.* 1999, 64, 8051-8053; Choi, S.; Koo, S. *J. Org. Chem.* 2005, 70, 3328-3331; Guha, S. K.; Koo, S. *J. Org. Chem.* 2005, 70, 9662-9665).

The above sulfone-mediated processes for the carotenoid syntheses feature the following advantages in that the stable intermediate sulfone compounds are formed through the processes, which can be easily purified by recrystallization. Furthermore, biologically more active all-(E)-carotenoids can be produced stereoselectively by the dehydrosulfonylation reaction, in which the by-product, the sodium salt of benzenesulfinic acid can be easily removed from the reaction mixture by just washing with water.

However, the above sulfone-mediated carotenoid syntheses still need to be improved especially in the number of steps and the preparation procedures for the required $C_{15}$ and $C_{10}$ compounds (D), (E), (F), (G) and (H). It was thus requested to devise a short and much efficient preparation method of the above intermediate sulfone compounds in order to have an expeditious and practical synthetic method of lycopene and β-carotene with great economical values.

SUMMARY OF INVENTION

Technical Problem

In order to fulfill the above requests, we have extensively studied the sulfone-mediated processes for the carotenoid synthesis. We devised a novel compound and the highly efficient synthetic method of lycopene and β-carotene utilizing the above novel compound, which are described in the present invention. Thus, the technical object of the present invention is to provide a novel dialdehyde compound and the preparation method of the same in order to efficiently and expeditiously synthesize the carotenoid compounds by the use of the sulfone chemistry. Another technical object of the present invention is to provide an improved synthetic process for preparing lycopene (Chemical Formula 1) with practical and economical values by employing the above novel dialdehyde compound. Still another technical object of the present invention is to provide an improved synthetic process for preparing β-carotene (Chemical Formula 2) with practical and economical values by employing the above novel dialdehyde compound.

Technical Solution

The first technical object of the present invention is achieved by the novel dialdehyde, 8-arenesulfonyl-2,6,11,15-tetramethyl-2,6,10,14-hexadecatetraenedial, represented by the Chemical Formula 3.

Chemical Formula 3

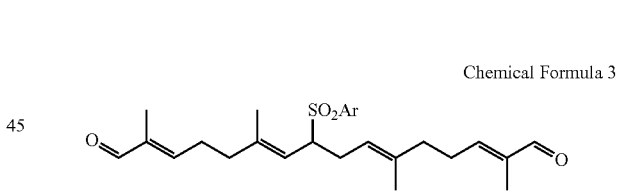

In the formula, Ar represents the groups of $C_6$-$C_{30}$ substituted or unsubstituted aryl, or $C_2$-$C_{30}$ substituted or unsubstituted heteroaryl.

The second technical object of the present invention is achieved by a process for preparing 8-arenesulfonyl-2,6,11,15-tetramethyl-2,6,10,14-hexadecatetraenedial of the Chemical Formula 3, which comprises the steps of (a-1) deprotonating geranyl sulfone (I), and then reacting with geranyl halide to give the $C_{20}$ sulfone compound (J); (b-1) oxidizing the above compound (J) both at the terminal allylic positions to produce the $C_{20}$ diol compound (K); and finally (c-1) oxidizing the above diol compound (K) to the novel $C_{20}$ dialdehyde (Scheme 3).

Scheme 3

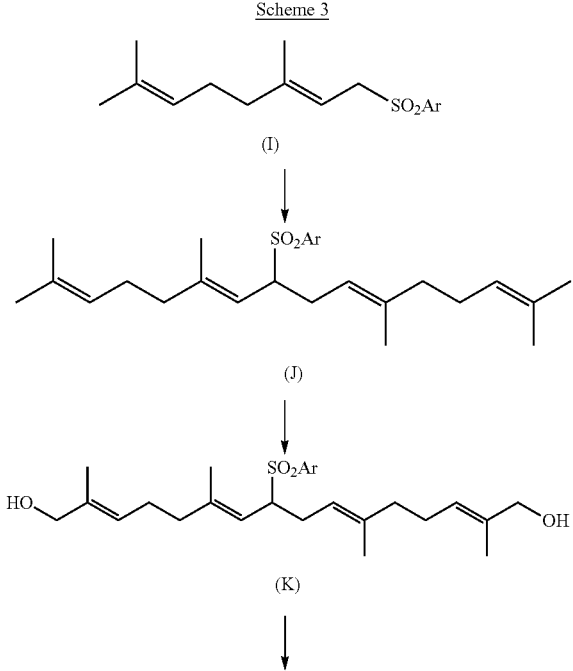

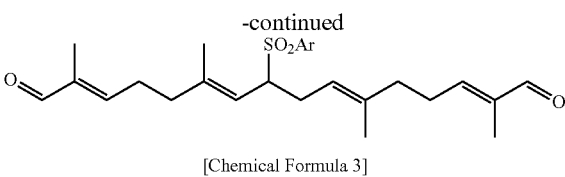

[Chemical Formula 3]

In the above formulas, Ar is defined as before.

The third technical object of the present invention is achieved by a process for preparing lycopene of the Chemical Formula 1, which comprises the steps of (a-2) de-protonating geranyl sulfone (I), and then reacting with the $C_{20}$ dialdehyde of the Chemical Formula 3 to synthesize the $C_{40}$ diol compound (L); (b-2) applying functional group transformation reactions to the above $C_{40}$ diol compound (L) to produce the corresponding dihalide or diether compound (M); and finally (c-2) reacting the above protected diol compound (M) with a base to induce the double elimination reactions of the sulfone and the halogen or the ether functional groups, thereby producing the conjugated polyene chain (Scheme 4).

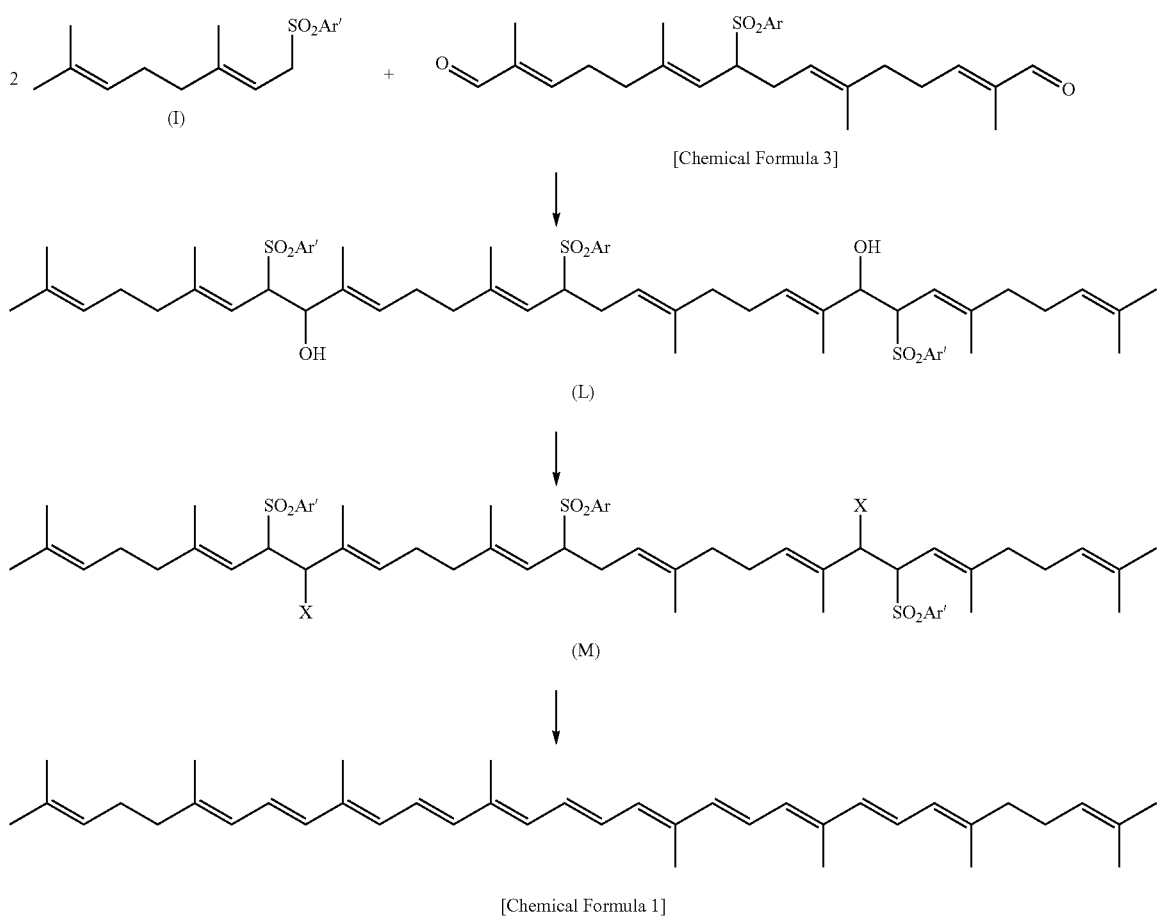

In the above formulas, Ar and Ar' independently represent the groups of $C_6$-$C_{30}$ substituted or unsubstituted aryl, or $C_2$-$C_{30}$ substituted or unsubstituted heteroaryl; X represents the groups of halogen atom or $C_1$-$C_{20}$ substituted or unsubstituted alkoxy.

The fourth technical object of the present invention is achieved by a process for preparing β-carotene of the Chemical Formula 2, which comprises the steps of (a-3) deprotonating cyclic geranyl sulfone (N), and then reacting with the $C_{20}$ dialdehyde of the Chemical Formula 3 to synthesize the $C_{40}$ diol compound (O); (b-3) applying functional group transformation reactions to the above $C_{40}$ diol compound (O) to produce the corresponding dihalide or diether compound (P); and finally (c-3) reacting the above protected diol compound (P) with a base to induce the double elimination reactions of the sulfone and the halogen or the ether functional groups, thereby producing the conjugated polyene chain (Scheme 5).

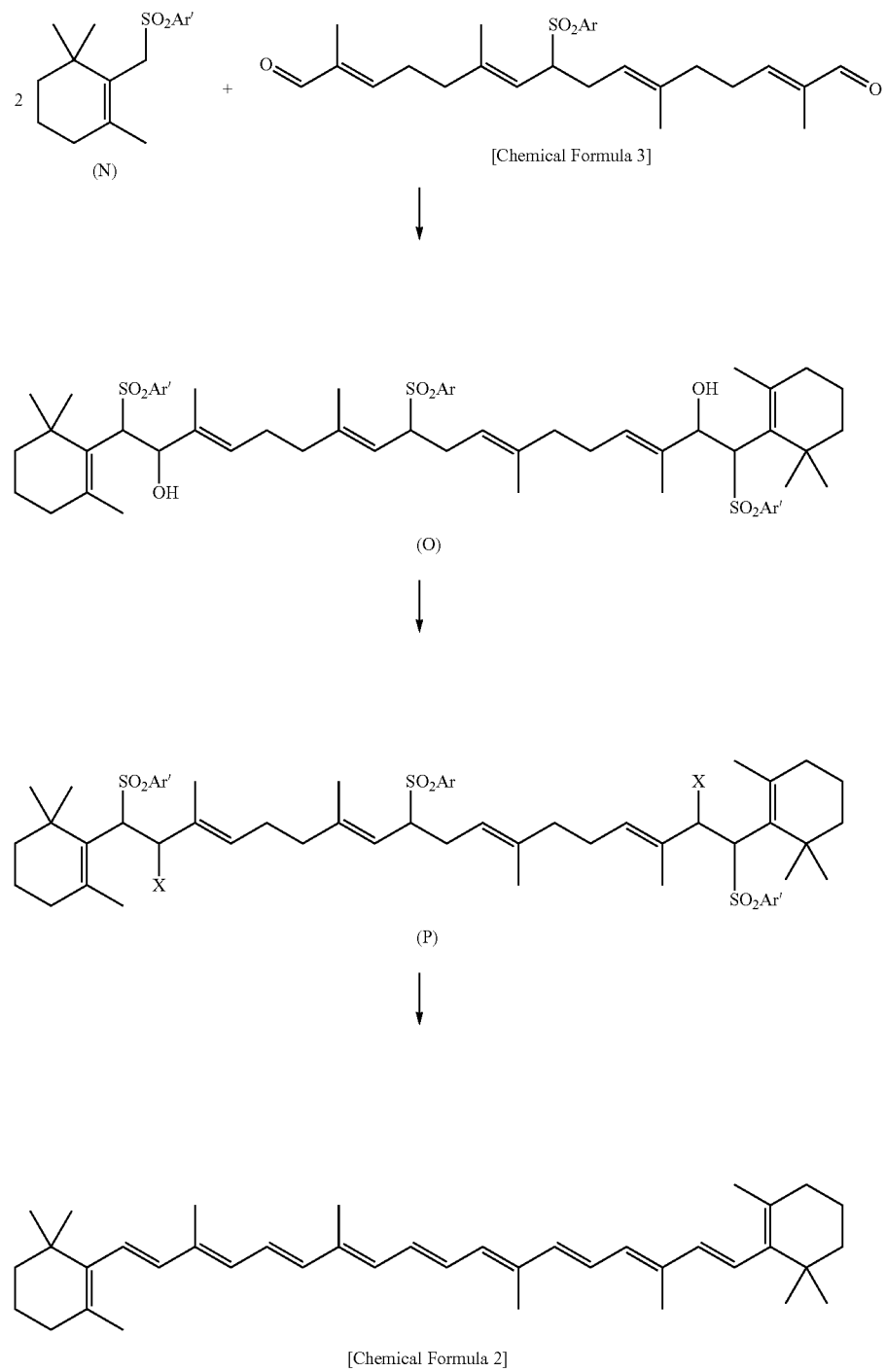

In the above formulas, Ar, Ar', and X are defined as before.

DETAILED DESCRIPTION OF THE INVENTION

According to the present invention, the $C_{20}$ dialdehyde compound of the Chemical Formula 3 is newly devised to efficiently produce the conjugated polyene chain of carotenoids by the sulfone-mediated coupling and elimination reactions, and is expeditiously and economically synthesized from readily available starting materials as the following process in Scheme 3.

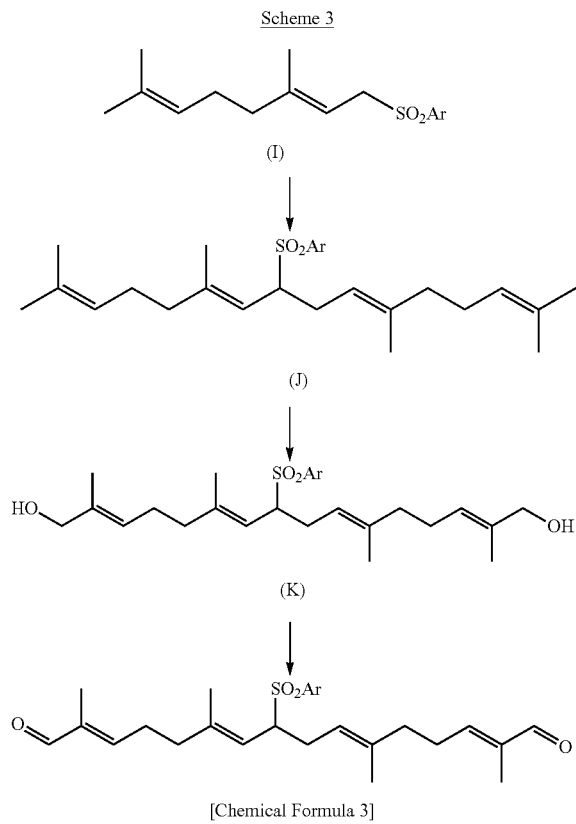

[Chemical Formula 3]

In the above formulas, Ar is defined as before.

Geranyl sulfone (I) can be deprotonated in THF using the base selected from alkyllithium such as n-BuLi, s-BuLi, t-BuLi, $CH_3Li$ or the Grignard reagent such as $CH_3MgBr$, EtMgBr, BuMgBr, $Et_2Mg$, $Bu_2Mg$, or metal alkoxide such as t-BuOK, EtONa, MeOK, and then reacted with geranyl halide to give the $C_{20}$ sulfone compound (J). This coupling reaction proceeds smoothly at the temperatures between −78° C. and 0° C., and geranyl bromide or geranyl chloride can be used as the electrophilic geranyl halide. When t-BuOK is used as a base, it is more appropriate to run the coupling reaction at the temperatures between −40° C. and 0° C., preferably at −20° C. in DMF as a solvent.

Since the allylic oxidation reaction of the above $C_{20}$ sulfone compound (J) should be regio and stereoselective to produce the bis(allylic alcohol) compound (K) with E-configurations, the conditions using $SeO_2$ and t-BuOOH as oxidants were selected (Umbreit, M. A.; Sharpless, K. B. *J. Am. Chem. Soc.* 1977, 99, 5526-5528). The oxidations should be proceeded both at the terminal allylic positions of the compound (J). When a catalytic amount of $SeO_2$ was used, the mono-allylic alcohol (the mono-oxidation product) was obtained as a major product regardless of the amount of t-BuOOH, while a significant amount of the starting compound (J) was recovered with less than one equivalent of t-BuOOH. The $C_{20}$ dialdehyde compound of the Chemical Formula 3 can be directly obtained by the oxidations of the compound (J) using excess oxidants (more than two equivalents of each oxidant, $SeO_2$ and t-BuOOH) at room temperature, however, the yield of the desired $C_{20}$ dialdehyde never reached to 20%, and highly polar side products were obtained as major products. Therefore, it was more appropriate to run the oxidation reaction at the temperatures between −10° C. and 10° C., preferably at 0° C. with excess oxidants (for example, more than 2 equivalents of $SeO_2$ and more than 4 equivalents of t-BuOOH) to synthesize the bis(allylic alcohol) compound (K) as the major product.

The oxidation reaction of the bis(allylic alcohol) compound (K) produce the $C_{20}$ dialdehyde of the Chemical Formula 3, in which various conditions can be utilized such as the Swern oxidation (DMSO/oxaly chloride/$Et_3N$), $MnO_2$, PCC (pyridinium chlorochromate), and PDC (pyridinium dichromate).

In order to efficiently synthesize the $C_{20}$ dialdehyde compound of the Chemical Formula 3, it is necessary to run the allylic oxidation reaction of the $C_{20}$ coupling product (J) at 0° C. using $SeO_2$ and t-BuOOH, and then to oxidize the resulting reaction mixture by the Swern oxidation without purification of the initial oxidation product, the bis(allylic alcohol) compound (K). This increases the yield of the $C_{20}$ dialdehyde of the Chemical Formula 3 by converting the hydroxy-aldehyde, the further oxidation product in the initial oxidation step into the desired $C_{20}$ dialdehyde in the Swern oxidation step.

According to the present invention, lycopene, represented by the Chemical Formula 1, can be efficiently and economically synthesized by the coupling reaction of the above $C_{20}$ dialdehyde of the Chemical Formula 3 with two equivalents of geranyl sulfone (I) and the double elimination reaction as the following process in Scheme 4.

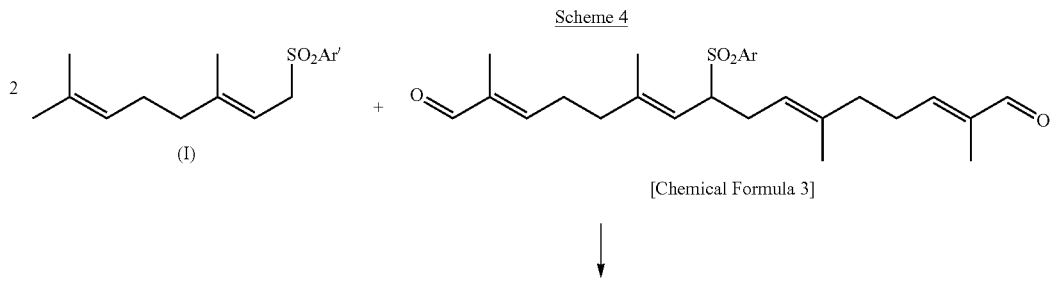

[Chemical Formula 3]

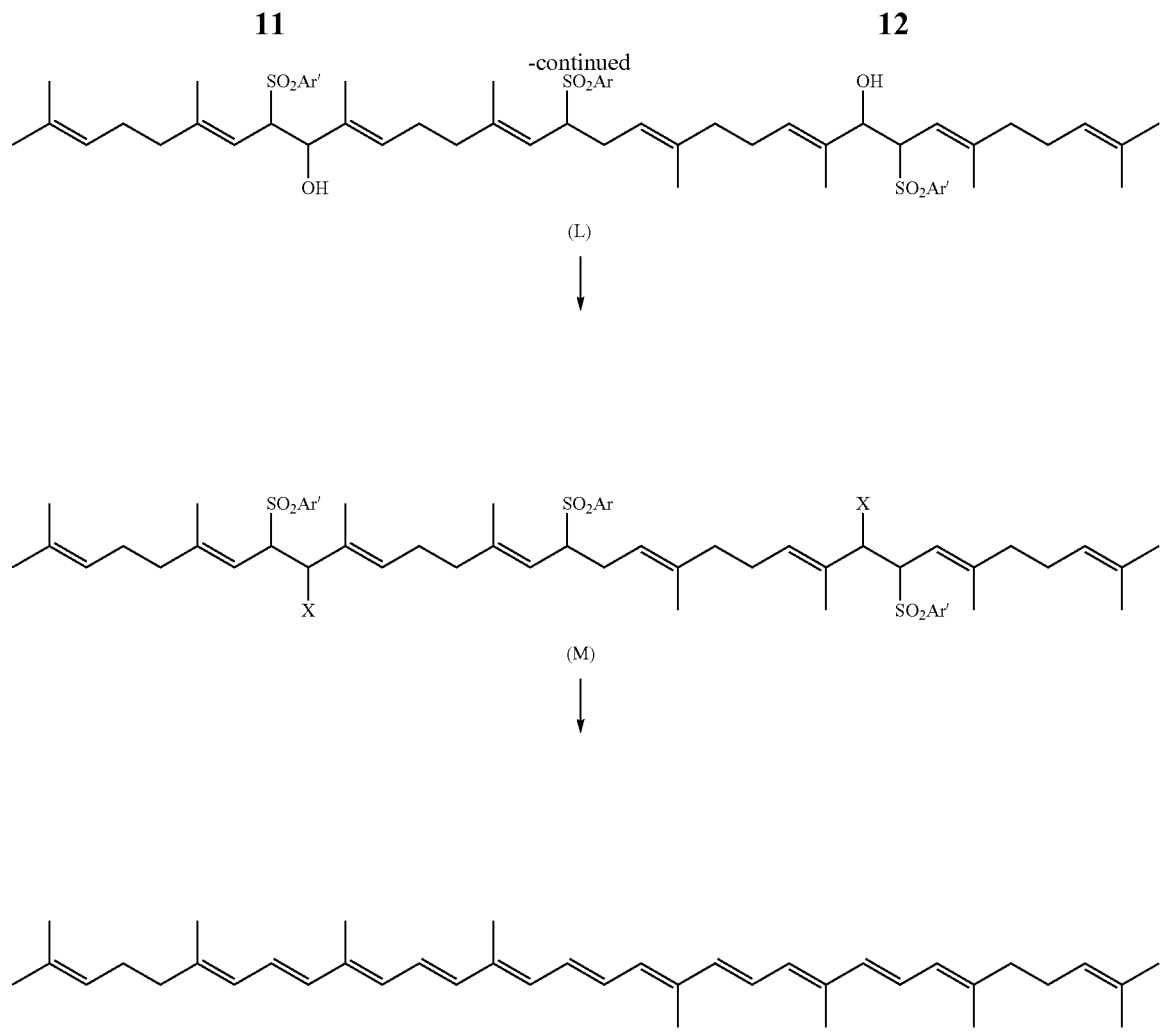

[Chemical Formula 1]

In the above formulas, Ar, Ar', and X are defined as before.

Geranyl sulfone (I) can be deprotonated using the base selected from alkyllithium such as n-BuLi, s-BuLi, t-BuLi, $CH_3Li$ or the Grignard reagent such as $CH_3MgBr$, EtMgBr, BuMgBr, $Et_2Mg$, $Bu_2Mg$, or metal amide such as LDA, MDA, LHMDS, NaHMDS, and then reacted with the above dialdehyde of the Chemical Formula 3 to provide the diol compound (L) containing the required carbon skeleton for the lycopene synthesis. The above coupling reaction should be carried out at the temperatures below −20° C., and quenched by adding a proton ($H^+$) source at the same temperature. Geranyl sulfone (I) and the dialdehyde of the Chemical Formula 3 can be regenerated from the coupling product (L) by the retro-aldol type reaction at the temperatures higher than −20° C.

The diol of the above $C_{40}$ coupling product (L) can be protected by transforming either to halides or to ethers under acidic conditions. The $C_{40}$ diol (L) reacted with $(COCl)_2$, $SOCl_2$ or $PBr_3$ in the presence of pyridine to give the corresponding dichloride or the dibromide (M-1), respectively. On the other hand, the etherification reactions with 3,4-dihydro-2H-pyran or ethyl vinyl ether in the presence of p-toluenesulfonic acid or 10-camphorsulfonic acid catalyst produced the corresponding THP or EOE ethers (M-2 and M-3, respectively) of the $C_{40}$ diol (L). The MOM protection (M-4) of the $C_{40}$ diol (L) can be carried out by the reaction with dimethoxymethane in the presence of $P_2O_5$.

Finally, the double elimination reaction, which has been utilized in the synthesis of retinol by Otera (Otera, J.; Misawa, H.; Onishi, T.; Suzuki, S.; Fujita, Y. *J. Org. Chem.* 1986, 51, 3834-3838), can be applied for the protected $C_{40}$ compounds (M) to give rise to lycopene. The double elimination reaction can be carried out using the metal alkoxide base such as MeOK, EtOK, t-BuOK, MeONa, EtONa, and t-BuONa in the solvent selected from cyclohexane, hexane, THF, dioxane, benzene, toluene, and xylenes at the temperatures between 25° C. to 150° C. It is desirable to carry out the reaction at the temperatures higher than 60° C. in order to produce the conjugated polyene chain of (E)-configurations by thermal isomerization. The double elimination reaction of the compound (M) removed the arenesulfonyl groups ($Ar'SO_2$ and $ArSO_2$) and the group X's, representing halide or ether functional groups, at the same time to produce the fully conjugated polyene chain of lycopene, represented by the Chemical Formula 1.

According to the present invention, β-carotene, represented by the Chemical Formula 2, can be efficiently and economically synthesized by the coupling reaction of the above $C_{20}$ dialdehyde of the Chemical Formula 3 with two equivalents of cyclic geranyl sulfone (N) and the double elimination reaction as the following process in Scheme 5.

Scheme 5

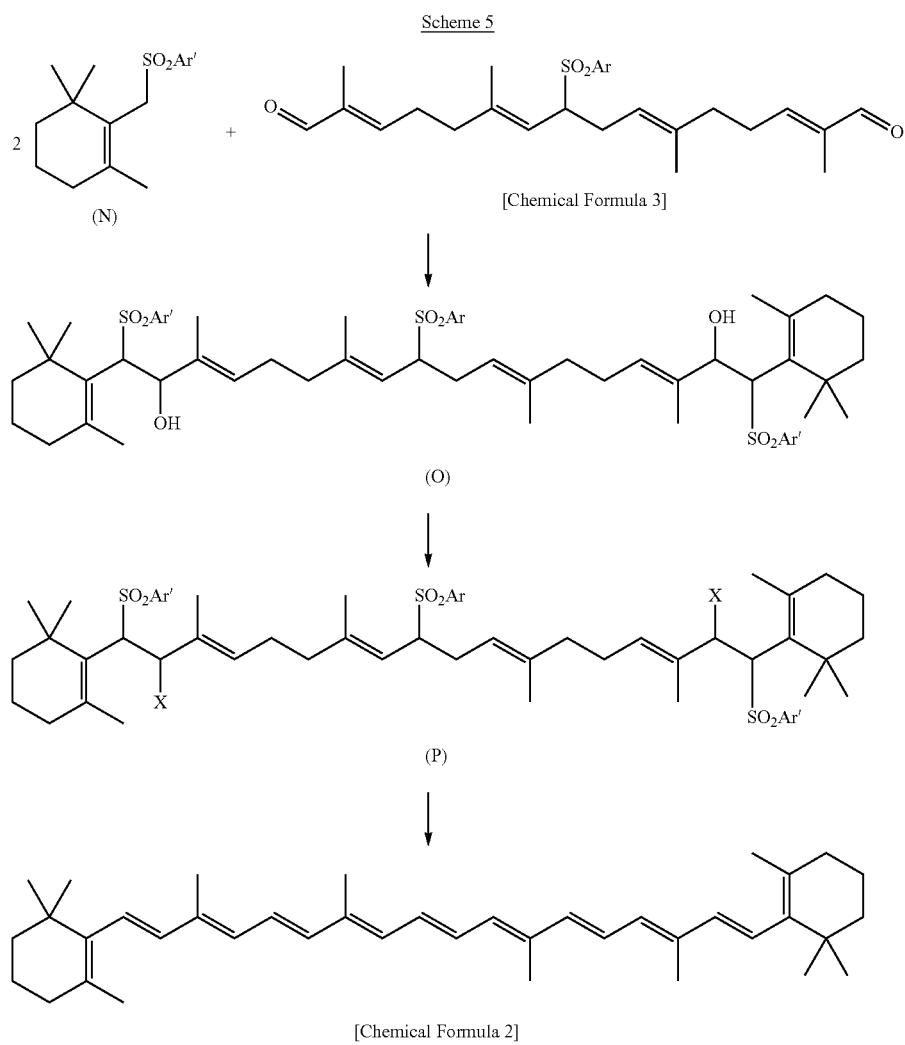

In the above formulas, Ar, Ar', and X are defined as before.

Cyclic geranyl sulfone (N) can be deprotonated using the base selected from alkyllithium such as n-BuLi, s-BuLi, t-BuLi, $CH_3Li$ or the Grignard reagent such as $CH_3MgBr$, EtMgBr, BuMgBr, $Et_2Mg$, $Bu_2Mg$, or metal amide such as LDA, MDA, LHMDS, NaHMDS, and then reacted with the above dialdehyde of the Chemical Formula 3 to provide the diol compound (O) containing the required carbon skeleton for the β-carotene synthesis. The above coupling reaction should be carried out at the temperatures below −20° C., and quenched by adding a proton ($H^+$) source at the same temperature. Cyclic geranyl sulfone (N) and the dialdehyde of the Chemical Formula 3 can be regenerated from the coupling product (O) by the retro-aldol type reaction at the temperatures higher than −20° C.

The diol of the above $C_{40}$ coupling product (O) can be protected by transforming either to halides or to ethers under acidic conditions. The $C_{40}$ diol (O) reacted with $(COCl)_2$, $SOCl_2$ or $PBr_3$ in the presence of pyridine to give the corresponding dichloride or the dibromide (P-1), respectively. On the other hand, the etherification reactions with 3,4-dihydro-2H-pyran or ethyl vinyl ether in the presence of p-toluenesulfonic acid or 10-camphorsulfonic acid catalyst produced the corresponding THP or EOE ethers (P-2 and P-3, respectively) of the $C_{40}$ diol (O). The MOM protection (P-4) of the $C_{40}$ diol (O) can be carried out by the reaction with dimethoxymethane in the presence of $P_2O_5$.

Finally, the double elimination reaction can be applied for the protected $C_{40}$ compounds (P) to give rise to β-carotene. The double elimination reaction can be carried out using the metal alkoxide base such as MeOK, EtOK, t-BuOK, MeONa, EtONa, and t-BuONa in the solvent selected from cyclohexane, hexane, THF, dioxane, benzene, toluene, and xylenes at the temperatures between 25° C. to 150° C. It is desirable to carry out the reaction at the temperatures higher than 60° C. in order to produce the conjugated polyene chain of (E)-configurations by thermal isomerization. The double elimination reaction of the compound (P) removed the arenesulfonyl groups ($Ar'SO_2$ and $ArSO_2$) and the group X's, representing halide or ether functional groups, at the same time to produce the fully conjugated polyene chain of β-carotene, represented by the Chemical Formula 2.

According to the present invention, the aryl groups in the definition of the compounds are aromatic cyclic systems, which include the cases where more than two cyclic structures are coupled or fused. The heteroaryl groups in the definition of the compounds denote the aryl groups, in which one or more of the carbon atoms is(are) replaced by an atom or atoms selected from N, O, S, and P. One or more of the hydrogen atoms in the above aryl or heteroaryl groups can be replaced by a group or groups selected independently from F, Cl, Br, CN, $NO_2$, OH; unsubstituted or F—, Cl—, Br—, CN—, $NO_2$— or HO-substituted $C_1$-$C_{20}$ alkyl; unsubstituted or F—, Cl—, Br—, CN—, $NO_2$— or HO-substituted $C_1$-$C_{20}$ alkoxy; unsubstituted or $C_1$-$C_{20}$ alkyl, $C_1$-$C_{20}$ alkoxy, F—, Cl—, Br—, CN—, $NO_2$— or HO-substituted $C_6$-$C_{30}$ aryl; unsubstituted or $C_1$-$C_{20}$ alkyl, $C_1$-$C_{20}$ alkoxy, F—, Cl—, Br—, CN—, $NO_2$— or HO-substituted $C_2$-$C_{30}$ heteroaryl; unsubstituted or $C_1$-$C_{20}$ alkyl, $C_1$-$C_{20}$ alkoxy, F—, Cl—, Br—, CN—, $NO_2$— or HO-substituted $C_5$-$C_{20}$ cycloalkyl; and unsubstituted or $C_1$-$C_{20}$ alkyl, $C_1$-$C_{20}$ alkoxy, F—, Cl—, Br—, CN—, $NO_2$— or HO-substituted $C_5$-$C_{30}$ heterocycloalkyl. Preferably, the substituent(s) is(are) selected from the groups of $C_1$-$C_5$ alkyl, halogen, $C_1$-$C_5$ alkoxy, OH, $NH_2$, and $NO_2$.

More specifically, the substituents Ar and Ar' of the compounds according to the present invention are independently selected from the groups of phenyl, $C_1$-$C_{10}$ alkylphenyl, $C_1$-$C_{10}$ alkoxyphenyl, halophenyl, cyanophenyl, dicyanophenyl, trifluo-romethoxyphenyl, o-, m-, or p-tolyl, o-, m-, or p-cumenyl, mesityl, phenoxyphenyl, (α,α-dimethylbenzene)phenyl, (N,N'-dimethyl)aminophenyl, (N,N'-diphenyl)aminophenyl, ($C_1$-$C_{10}$ alkylcyclohexyl)phenyl, biphenyl, $C_1$-$C_{10}$ alkylbiphenyl, $C_1$-$C_{10}$ alkoxybiphenyl, pentarenyl, indenyl, naphthyl, $C_1$-$C_{10}$ alkylnaphthyl, $C_1$-$C_{10}$ alkoxynaphthyl, halonaphthyl, cyanonaphthyl, biphenylrenyl, $C_1$-$C_{10}$ alkylbiphenylrenyl, $C_1$-$C_{10}$ alkoxybiphenylrenyl, anthracenyl, $C_1$-$C_{10}$ alkylanthracenyl, $C_1$-$C_{10}$ alkoxyanthracenyl, azurenyl, heptarenyl, acenaphthylrenyl, phenarenyl, fluorenyl, methylanthryl, phenanthrenyl, triphenylrenyl, pirenyl, crycenyl, ethylcrycenyl, picenyl, perylrenyl, chloroperylrenyl, pentaphenyl, pentacenyl, tetraphenylrenyl, hexaphenyl, hexacenyl, rubicenyl, coronenyl, trinaphthylrenyl, heptaphenyl, heptacenyl, piranthrenyl, obarenyl, carbazolyl, $C_1$-$C_{10}$ alkylcarbazolyl, thiophenyl, indolyl, purinyl, benzimidazolyl, quinolinyl, benzothiophenyl, parathiazinyl, pyrrolyl, pyrazolyl, imidazolyl, imidazolinyl, oxazolyl, thiazolyl, triazolyl, tetrazolyl, oxadiazolyl, pyridinyl, pyridazinyl, pyrimidinyl, pyrazinyl, and thianthrenyl. However, the selection is not restricted to the above examples by any means.

The $C_1$-$C_{20}$ substituted or unsubstituted alkoxy group in the substituent of the compounds according to the present invention can be branched or strait hydrocarbons containing the R—O (alkyl-oxygen) moiety. The groups of THPO (tetrahydropyranyloxy), EEO (1-ethoxyethoxy), and MOMO (methoxymethoxy) are preferable examples. One or more of the hydrogen atoms in the above alkoxy group can be replaced in the same pattern as the hydrogen(s) of the above aryl groups.

EXAMPLES

The invention is described in more detail by referring to the examples below, but it should be noticed that those examples are described only to specifically describe the present invention, so that the present invention is not restricted to the examples by any means.

Example 1

8-Benzenesulfonyl-2,6,11,15-tetramethyl-2,6,10,14-hexadecatetraenedial (J)

To a stirred solution of geranyl sulfone (I) (5.00 g 17.93 mmol) in DMF (50 mL) at −20° C. was added t-BuOK (2.33 g, 19.72 mmol). The resulting orange mixture was stirred at that temperature for 30 min, and a solution of geranyl bromide (4.28 g, 19.72 mmol) in DMF (10 mL) was added. The mixture was stirred at −20° C. for 1 h, and quenched with 1 M HCl solution (20 mL). The mixture was extracted with EtOAc (50 mL), washed with 1 M HCl (10 mL×3), dried over anhydrous $Na_2SO_4$, filtered, and concentrated under reduced pressure. The crude product was purified by silica gel column chromatography to give the coupling product (J) (7.10 g, 17.12 mmol) in 95% yield.

$^1$H NMR (300.40 MHz, CDCl.sub.3) δ 1.19 (d, J=1.3 Hz, 3H), 1.57 (s, 3H), 1.59 (s, 3H), 1.60 (s, 3H), 1.65 (s, 3H), 1.68 (s, 3H), 1.90-2.07 (m, 8H), 2.35 (ddd, J=14.0, 10.9, 7.4 Hz, 1H), 2.89 (ddd, J=14.0, 7.2, 3.3 Hz, 1H), 3.73 (ddd, J=10.9, 10.5, 3.3 Hz, 1H), 4.97 (t, J=7.3 Hz, 1H), 5.02 (d, J=10.5 Hz, 1H), 7.47-7.55 (m, 2H), 7.58-7.66 (m, 1H), 7.82-7.88 (m, 2H) ppm.

$^{13}$C NMR (75.45 MHz, CDCl.sub.3) δ 16.3, 16.4, 17.6, 17.6, 25.6, 25.6, 26.2, 26.3, 26.5, 39.6, 39.6, 64.7, 116.9, 118.5, 123.5, 123.9, 128.6, 129.1, 131.4, 131.9, 133.3, 138.0, 138.5, 145.1 ppm.

IR (KBr) 2917, 1447, 1304, 1146, 1085 $cm^{-1}$.

HRMS ($FAB^+$) m/z calcd for $C_{26}H_{39}O_2S$ 415.2671, found 415.2665.

Example 2

8-Benzenesulfonyl-2,6,11,15-tetramethyl-2,6,10,14-hexadecatetraene-1,16-diol (K)

To a stirred suspension of $SeO_2$ (0.54 g, 4.82 mmol, 2 equiv) and salicylic acid (0.34 g, 2.41 mmol, 1 equiv) in $CH_2Cl_2$ (20 mL) at 0° C. was added a 3.0 M solution of t-butyl hydrogen peroxide (TBHP) in toluene (5.0 mL, 14.46 mmol, 6 equiv). The mixture was stirred at that temperature for 1.5 h, and a solution of the compound (J) (1.00 g, 2.41 mmol, 1 equiv) in CH.sub.2Cl.sub.2 (5 mL) was slowly added for 10 min. The reaction mixture was stirred at 0° C. for 3 h, diluted with $CH_2Cl_2$ (30 mL), washed with 10% NaOH solution (10 mL×3) and then saturated $Na_2S_2O_3$ solution (10 mL×3), dried over anhydrous $Na_2SO_4$, filtered, and concentrated under reduced pressure. The crude product was purified by silica gel column chromatography to give the diol compound (K) (0.47 g, 1.06 mmol) in 44% yield, together with the hydroxylaldehyde (0.13 g, 0.29 mmol, 12% yield), which was derived from further oxidation. Both of these two compounds can provide the dialdehyde of the Chemical Formula 3 after the Swern oxidation reaction.

$^1$H NMR (300.40 MHz, $CDCl_3$) δ 1.24 (d, J=1.3 Hz, 3H), 1.58 (s, 3H), 1.63 (s, 3H), 1.65 (s, 3H), 1.92-2.24 (m, 8H), 2.36 (ddd, J=14.3, 10.0, 7.3 Hz, 1H), 2.77 (ddd, J=14.3, 7.4, 3.7 Hz, 1H), 3.76 (ddd, J=10.3, 10.0, 3.7 Hz, 1H), 3.95 (s, 2H), 3.97 (s, 2H), 5.00 (d, J=10.3 Hz, 1H), 5.00 (t, J=7.3 Hz, 1H), 5.33 (br s, 2H), 7.48-7.67 (m, 3H), 7.80-7.89 (m, 2H) ppm.

$^{13}$C NMR (75.45 MHz, CDCl.sub.3) δ 13.6, 13.6, 16.1, 16.4, 25.4, 25.8, 26.7, 39.1, 39.2, 64.6, 68.5, 68.6, 116.9, 118.8, 124.6, 125.2, 128.7, 128.9, 133.4, 134.8, 135.3, 137.9, 138.1, 144.8 ppm.

IR (KBr) 3413, 1447, 1301, 1144, 1084, 1013 $cm^{-1}$.

HRMS ($CI^+$) m/z calcd for $C_{26}H_{39}O_4S$ 447.2569, found 447.2568.

Example 3

8-Benzenesulfonyl-2,6,11,15-tetramethyl-2,6,10,14-hexadecatetraenedial (Chemical Formula 3)

Method A: Oxidation from the Compound (K)

To a stirred solution of the diol compound (K) (0.30 g, 0.68 mmol) in $CH_2Cl_2$ (20 mL) was added $MnO_2$ (1.77 g, 20.4 mmol). The mixture was stirred at room temperature for 48 h, and filtered. The filter cake was rinsed with $CH_2Cl_2$, and the combined organic layer was concentrated under reduced pressure. The crude product was purified by silica gel column chromatography to give the dialdehyde of the Chemical Formula 3 (0.18 g, 0.41 mmol) in 60% yield.

Method B: Oxidation from the Compound (J) Through the Compound (K)

To a stirred suspension of $SeO_2$ (0.54 g, 4.82 mmol, 2 equiv) and salicylic acid (0.34 g, 2.41 mmol, 1 equiv) in MeCN (15 mL) at 0° C. was added a 3.0 M solution of TBHP in toluene (5.0 mL, 14.46 mmol, 6 equiv). The mixture was stirred at that temperature for 1.5 h, and a solution of the compound (J) (1.00 g, 2.41 mmol, 1 equiv) in MeCN (5 mL) was slowly added for 10 min. The reaction mixture was stirred at 0° C. for 3 h, diluted with EtOAc (30 mL), washed with 10% NaOH solution (10 mL.times.3) and then saturated $Na_2S_2O_3$ solution (10 mL×3), dried over anhydrous $Na_2SO_4$, filtered, and concentrated under reduced pressure to give the crude allylic oxidation product (1.50 g).

Method C: Direct Oxidation from (J)

To a stirred suspension of $SeO_2$ (2.14 g, 19.27 mmol, 2 equiv) in $CH_2Cl_2$ (35 mL) was added a 70% aqueous solution of TBHP (5.3 mL, 38.6 mmol, 4 equiv). The mixture was stirred at room temperature for 30 min, and a solution of the compound (J) (4.00 g, 9.64 mmol, 1 equiv) in $CH_2Cl_2$ (5 mL) was slowly added. The reaction mixture was stirred at room temperature for 14 h, diluted with EtOAc (60 mL), washed with 1 M NaOH solution (20 mL.times.3) and then saturated $Na_2S_2O_3$ solution (20 mL×3), dried over anhydrous $Na_2SO_4$, filtered, and concentrated under reduced pressure. The crude product was purified by silica gel column chromatography to give the dialdehyde of the Chemical Formula 3 (0.73 g, 1.59 mmol) in 16% yield.

$^1$H NMR (300.40 MHz, $CDCl_3$) δ 1.27 (d, J=1.3 Hz, 3H), 1.63 (s, 3H), 1.72 (d, J=1.1 Hz, 3H), 1.73 (d, J=0.9 Hz, 3H), 2.15 (t, J=7.4 Hz, 4H), 2.30-2.46 (m, 5H), 2.86 (ddd, J=14.4, 7.2, 3.7 Hz, 1H), 3.77 (ddd, J=10.3, 10.3, 3.7 Hz, 1H), 5.02 (dt, $J_d$=1.1, $J_t$=7.4 Hz, 1H), 5.06 (dd, J=10.3, 1.2 Hz, 1H), 6.39 (dt, $J_d$=1.3, J=7.0 Hz, 1H), 6.41 (dt, $J_d$=1.3, $J_t$=7.2 Hz, 1H), 7.48-7.68 (m, 3H), 7.81-7.87 (m, 2H), 9.36 (s, 1H), 9.38 (s, 1H) ppm.

$^{13}$C NMR (75.45 MHz, $CDCl_3$) δ 9.2, 9.2, 16.2, 16.4, 26.7, 26.9, 27.1, 37.9, 38.0, 64.4, 118.0, 119.7, 128.8, 128.9, 133.5, 137.2, 137.9, 139.4, 139.6, 143.8, 152.8, 153.7, 194.8, 195.0 ppm.

IR (KBr) 2944, 1686, 1447, 1303, 1145, 1084 $cm^{-1}$.

HRMS (FAB$^+$) m/z calcd for $C_{26}H_{35}O_4S$ 443.2256, found 443.2248.

Example 4

8,16,25-Tris(benzenesulfonyl)-2,6,10,14,19,23,27,31-octamethyl-2,6,10,14,1-8,22,26,30-dotriacontaoctaene-9,24-diol (L)

To a stirred solution of geranyl phenyl sulfone (I) (2.41 g, 8.65 mmol, 2.2 equiv) in THF (30 mL) at −78° C. was added 1.6 M solution of n-BuLi in hexane (6.14 mL, 9.83 mmol, 2.5 equiv). The resulting orange solution was stirred at that temperature for 1 h, and a solution of the dialdehyde of the Chemical Formula 3 (1.74 g, 3.93 mmol, 1 equiv) in THF (10 mL) was added for 5 min. The resulting mixture was stirred at −78° C. for 1 h, and quenched with 1 M HCl solution (10 mL). The mixture was warmed to room temperature, extracted with EtOAc (30 mL×2), washed with 1 M HCl solution (20 mL×2), dried over anhydrous $Na_2SO_4$, filtered, and concentrated under reduced pressure. The crude product was purified by silica gel column chromatography to give the $C_{40}$ diol compound (L) (3.65 g, 3.66 mmol) in 93% yield.

$^1$H NMR (300.40 MHz, $CDCl_3$) δ 1.07 (s, 3H), 1.12 (s, 3H), 1.19 (d, J=1.5 Hz, 3H), 1.45 (s, 3H), 1.47 (s, 3H), 1.56 (s, 6H), 1.58 (s, 3H), 1.67 (s, 3H), 1.68 (s, 3H), 1.80-2.07 (m, 16H), 2.24-2.40 (m, 1H), 2.77-2.90 (m, 1H), 3.71 (br t, J=9.5 Hz, 1H), 3.93 (dd, J=9.1, 7.0 Hz, 1H), 3.96 (dd, J=9.1, 6.6 Hz, 1H), 4.59 (d, J=9.2 Hz, 1H), 4.60 (d, J=8.9 Hz, 1H), 4.68 (d, J=10.1 Hz, 1H), 4.72 (d, J=9.0 Hz, 1H), 4.90-5.05 (m, 5H), 5.30-5.43 (m, 2H), 7.45-7.68 (m, 9H), 7.78-7.90 (m, 6H) ppm.

$^{13}$C NMR (75.45 MHz, $CDCl_3$) δ 10.5, 10.5, 13.0, 15.8, 15.9, 16.2, 16.4, 16.5, 17.6, 25.7, 25.7, 25.8, 26.0, 26.2, 26.2, 26.5, 39.0, 39.5, 39.8, 64.7, 67.7, 68.4, 72.4, 76.4, 112.0, 114.2, 117.1, 119.0, 123.3, 123.6, 128.7, 128.7, 128.8, 129.0, 129.1, 129.2, 129.3, 129.5, 130.1, 131.9, 132.0, 132.0, 133.1, 133.4, 133.6, 133.7, 133.9, 137.4, 138.1, 144.4, 144.5, 144.7 ppm.

IR (KBr) 3497, 2930, 1447, 1300, 1143, 1083 $cm^{-1}$.

HRMS (FAB$^+$) m/z calcd for $C_{46}H_{65}O_3S$ [$C_{58}H_{79}O_8S_3$-2($C_6H_6SO_2$)—$H_2O$] 697.4654. found 697.4645.

Example 5

9,24-Dibromo-8,16,25-tris(benzenesulfonyl)-2,6,10,14,19,23,27,31-octamethyl-1-2,6,10,14,18,22,26,30-dotriacontaoctaene (M-1)

To a stirred solution of the $C_{40}$ diol compound (L) (3.68 g, 3.69 mmol) in $CH_2Cl_2$ (50 mL) at 0° C. were added pyridine (1.5 mL, 18.45 mmol) and $PBr_3$ (0.43 mL, 4.42 mmol). The mixture was stirred at 0° C. for 1 h, diluted with $CH_2Cl_2$ (30 mL), washed with 1 M HCl solution (10 mL×3), dried over anhydrous $MgSO_4$, filtered, and concentrated under reduced pressure to give the di-bromination product (M-1) (3.99 g, 3.54 mmol) in 96% crude yield. This compound was not purified and directly utilized in the elimination reaction to produce lycopene (see Example 9-A).

$^1$H NMR (300.40 MHz, $CDCl_3$) δ 1.06-1.36 (m, 9H), 1.42-1.73 (m, 21H), 1.80-2.22 (m, 16H), 2.22-2.50 (m, 1H), 2.74-2.93 (m, 1H), 3.63-4.02 (m, 2H), 4.08-4.40 (m, 1H), 4.53-4.86 (m, 2H), 4.86-5.16 (m, 4H), 5.16-5.72 (m, 4H), 7.43-7.68 (m, 9H), 7.75-7.97 (m, 6H) ppm.

IR (KBr) 2920, 1663, 1447, 1375, 1304, 1145, 1083, 955 $cm^{-1}$.

HRMS (FAB$^+$) m/z calcd for $C_{52}H_{72}BrO_4S_2$ [$C_{58}H_{77}Br_2O_6S_3$—($C_6H_5SO_2$)—Br] 903.4055, found 903.4055.

Example 6

8,16,25-Tris(benzenesulfonyl)-2,6,10,14,19,23,27,31-octamethyl-2,6,10,14,1-8,22,26,30-dotriacontaoctaene-9,24-diol, bis(tetrahydropyranyl)ether (M-2)

To a stirred solution of the $C_{40}$ diol compound (L) (0.74 g, 0.74 mmol) in $CH_2Cl_2$ (30 mL) were added 3,4-dihydro-2H-pyran (0.35 mL, 3.7 mmol) and 10-camphorsulfonic acid (0.09 g, 0.37 mmol). The reaction mixture was stirred at room temperature for 14 h, diluted with $CH_2Cl_2$ (40 mL), washed with saturated $NaHCO_3$ solution (20 mL×2), dried over anhydrous $K_2CO_3$, filtered, and concentrated under reduced pressure. The crude product was purified by silica gel (deactivated by $Et_3N$) column chromatography to give the bis(tetrahydropyranyl)ether (M-2) (0.85 g, 0.73 mmol) in 98% yield.

$^1H$ NMR (300.40 MHz, $CDCl_3$) δ 1.02-1.22 (m, 9H), 1.32-1.71 (m, 21H), 1.71-1.83 (m, 12H), 1.83-2.08 (m, 16H), 2.26-2.40 (m, 1H), 2.68-2.83 (m, 1H), 3.32-3.61 (m, 2H), 3.61-3.90 (m, 2H), 4.06-4.38 (m, 3H), 4.48-4.55 (m, 2H), 4.72-5.10 (m, 8H), 5.30-5.52 (m, 2H), 7.41-7.66 (m, 9H), 7.77-7.91 (m, 6H) ppm.

IR (KBr) 2942, 1447, 1303, 1144, 1077, 1021 $cm^{-1}$.

HRMS ($FAB^+$) m/z calcd for $C_{46}H_{63}O_2S$ [$C_{68}H_{95}O_{10}S_3$-2($C_6H_6SO_2$)-2($C_5H_{10}O_2$)] 679.4549, found 679.4550.

Example 7

8,16,25-Tris(benzenesulfonyl)-2,6,10,14,19,23,27,31-octamethyl-2,6,10,14,1-8,22,26,30-dotriacontaoctaene-9,24-diol, bis(1-ethoxyethyl)ether (M-3)

To a stirred solution of the $C_{40}$ diol compound (L) (1.00 g, 1.00 mmol) in $CH_2Cl_2$ (10 mL) at 0° C. were added ethyl vinyl ether (0.80 mL, 8.00 mmol) and pyridinium p-toluenesulfonate (0.13 g, 0.50 mmol). The mixture was stirred at 0° C. for 1 h, and warmed to and stirred at room temperature for 14 h. The mixture was then diluted with $CH_2Cl_2$ (30 mL), washed with saturated $NaHCO_3$ (10 mL×3), dried over anhydrous $K_2CO_3$, filtered, and concentrated under reduced pressure. The crude product was purified by silica gel (deactivated by $Et_3N$) column chromatography to give the bis(1-ethoxyethyl)ether (M-3) (1.09 g, 0.84 mmol) in 95% yield.

$^1H$ NMR (300.40 MHz, $CDCl_3$) δ 1.00-1.42 (m, 24H), 1.43-1.74 (m, 18H), 1.76-2.10 (m, 16H), 2.25-2.46 (m, 1H), 2.78-2.95 (m, 1H), 3.24-3.44 (m, 11H), 3.44-3.62 (m, 1H), 3.62-3.85 (m 4H), 4.05-4.22 (m 1H), 4.45-4.90 (m, 5H), 4.90-5.10 (m, 5H), 5.27-5.52 (m 2H), 7.42-7.68 (m, 9H), 7.77-7.92 (m, 6H) ppm.

IR (KBr) 2929, 1447, 1305, 1146, 1093, 1026 $cm^{-1}$.

HRMS ($FAB^+$) m/z calcd for $C_{46}H_{63}O_2S_3$ [$C_{66}H_6O_{10}S_3$-2($C_6H_6SO_2$)-2($C_4H_{10}O_2$)] 679.4549, found 679.4536.

Example 8

8,16,25-Tris(benzenesulfonyl)-2,6,10,14,19,23,27,31-octamethyl-2,6,10,14,1-8,22,26,30-dotriacontaoctaene-9,24-diol, bis(methoxymethyl)ether (M-4)

To a stirred solution of the $C_{40}$ diol compound (L) (1.73 g, 1.73 mmol) in dimethoxy methane (6.2 mL, 40 equiv) at room temperature was added $P_2O_5$ (0.50 g, 3.46 mmol, 2 equiv). The resulting yellow solution was stirred for 9 h, and $P_2O_5$ (0.25 g, 1.73 mmol, 1 equiv) was added again. Stirring for another 3 h, the reaction mixture was diluted with toluene (40 mL), washed with saturated $NaHCO_3$ solution (10 mL×3), dried over anhydrous $Na_2SO_4$, filtered, and concentrated under reduced pressure. The crude product was purified by silica gel (deactivated by $Et_3N$) column chromatography to give the bis(methoxymethyl)ether (M-4) (1.71 g, 1.58 mmol) in 91% yield.

$^1H$ NMR (300.40 MHz, $CDCl_3$) δ 1.00 (s, 3H), 1.10-1.26 (m, 6H), 1.35-1.38 (m, 3H), 1.49-1.68 (m, 18H), 1.76-2.11 (m, 16H), 2.26-2.45 (m, 11H), 2.78-2.93 (m, 1H), 3.48 (s, 3H), 3.50 (s, 3H), 3.68-3.87 (m, 2H), 4.08-4.21 (m, 1H), 4.50-4.87 (m, 4H), 4.58 (s, 2H), 4.61 (s, 2H), 4.88-5.08 (m, 4H), 5.30-5.52 (m, 2H), 7.44-7.69 (m, 9H), 7.78-7.90 (m, 6H) ppm.

IR (KBr) 2917, 1447, 1303, 1145, 1025 $cm^{-1}$.

HRMS ($FAB^+$) m/z calcd for $C_{46}H_{63}O_2S$[$C_{62}H_{87}O_{10}S_3$-2($C_6H_6SO_2$)-2($C_2H_6O_2$)] 679.4549, found 679.4563.

Example 9

Lycopene (Chemical Formula 1)

Method A: Elimination Reaction from the Compound (M-1)

To a stirred suspension of the crude (see Example 5) $C_{40}$ dibromide compound (M-1) (0.31 g, 0.27 mmol) in cyclohexane (10 mL) and benzene (5 mL) was added KOMe (0.58 g, 8.27 mmol). The mixture was heated to 70~80° C. for 11 h, cooled to room temperature, and 1 M HCl (20 mL) was carefully added. The reaction mixture was extracted with a 9:1 (v:v) solution (60 mL) of hexane and benzene, dried over anhydrous $Na_2SO_4$, filtered, and concentrated under reduced pressure. The resulting red solid was diluted with hexane (30 mL) and washed with $CH_3CN$ (10 mL×3). The combined $CH_3CN$ solution was extracted again with hexanes. The hexane layers were combined and concentrated under reduced pressure to give Lycopene of the Chemical Formula 1 (0.11 g, 0.21 mmol) in 76% crude yield. The crude product was purified by recrystallization from MeOH and THF to provide all-(E)-Lycopene (0.083 g, 0.15 mmol) in 57% yield as a dark red crystal.

Method B: Elimination Reaction from the Compound (M-2)

To a stirred suspension of the bis(tetrahydropyranyl)ether (M-2) (0.44 g, 0.38 mmol) in cyclohexane (20 mL) and benzene (10 mL) was added KOMe (0.79 g, 11.3 mmol). The mixture was heated to 70~80° C. for 13 h, cooled to room temperature, and 1 M HCl (20 mL) was carefully added. The reaction mixture was extracted with a 9:1 (v:v) solution (40 mL) of hexane and benzene, dried over anhydrous $Na_2SO_4$, filtered, and concentrated under reduced pressure. The resulting red solid was diluted with hexane (30 mL) and washed with $CH_3CN$ (10 mL×3). The combined $CH_3CN$ solution was extracted again with hexanes. The hexane layers were combined and concentrated under reduced pressure to give Lycopene of the Chemical Formula 1 (0.20 g, 0.37 mmol) in 97% crude yield. The crude product was purified by recrystallization from MeOH and THF to provide all-(E)-Lycopene (0.16 g, 0.29 mmol) in 79% yield as a dark red crystal.

Method C: Elimination Reaction from the Compound (M-3)

To a stirred suspension of the bis(1-ethoxyethyl)ether (M-3) (0.70 g, 0.61 mmol) in cyclohexane (20 mL) and benzene (5 mL) was added KOMe (1.28 g, 18.30 mmol). The mixture was heated to 70~80° C. for 18 h, cooled to room temperature, and 1 M HCl (25 mL) was carefully added. The reaction mixture was extracted with a 9:1 (v:v) solution (50 mL) of hexane and benzene, dried over anhydrous $Na_2SO_4$, filtered, and concentrated under reduced pressure. The resulting red solid was diluted with hexane (30 mL) and washed with $CH_3CN$ (10 ml×3). The combined $CH_3CN$ solution was extracted again with hexanes. The hexane layers were combined and concentrated under reduced pressure to give Lycopene of the Chemical Formula 1 (0.24 g, 0.45 mmol) in 73% crude yield. The crude product was purified by recrystallization from MeOH and THF to provide all-(E)-Lycopene (0.17 g, 0.32 mmol) in 52% yield as a dark red crystal.

21

Method D: Elimination Reaction from the Compound (M-4)

To a stirred solution of the bis(methoxymethyl)ether (M-4) (1.67 g, 1.54 mmol) in cyclohexane (15 mL) and benzene (25 mL) was added KOMe (3.78 g, 53.9 mmol). The mixture was heated to 70~80° C. for 15 h, cooled to room temperature, and 1 M HCl (60 mL) was carefully added. The reaction mixture was extracted with a 9:1 (v:v) solution (60 mL) of hexane and benzene, dried over anhydrous $Na_2SO_4$, filtered, and concentrated under reduced pressure. The resulting red solid was diluted with hexane (30 mL) and washed with $CH_3CN$ (10 mL×3). The combined $CH_3CN$ solution was extracted again with hexanes. The hexane layers were combined and concentrated under reduced pressure to give Lycopene of the Chemical Formula 1 (0.61 g, 1.14 mmol) in 74% crude yield. The crude product was purified by recrystallization from MeOH and THF to provide all-(E)-Lycopene (0.46 g, 0.86 mmol) in 56% yield as a dark red crystal.

The $^1$H NMR spectra of all-(E)-Lycopene, which were prepared according to the above methods A-D, were identical to that of the authentic sample.

Example 10

1,9,18-Tris(benzenesulfonyl)-3,7,12,16-tetramethyl-1,18-bis(2,6,6-trimethyl-l-1-cyclohexen-1-yl)-3,7,11,15-octadecatetraene-2,17-diol (O)

To a stirred solution of β-cyclogeranyl phenyl sulfone (N) (0.46 g, 1.63 mmol) in THF (10 mL) at 0° C. was added 1.6 M solution of n-BuLi in hexane (1.22 mL, 1.97 mmol). The resulting orange solution was stirred at that temperature for 1 h, and cooled to −78° C. The solution of the dialdehyde of the Chemical Formula 3 (0.29 g, 0.66 mmol) in THF (5 mL) was then added for 5 min. The resulting mixture was stirred at −78° C. for 1 h, and quenched with 1 M HCl solution (5 mL). The mixture was warmed to room temperature, extracted with EtOAc (20 mL×2), washed with 1 M HCl solution (10 mL×2), dried over anhydrous $Na_2SO_4$, filtered, and concentrated under reduced pressure. The crude product was purified by silica gel column chromatography to give the $C_{40}$ diol compound (O) (0.56 g, 0.56 mmol) in 86% yield.

$^1$H NMR (300.40 MHz, CDCl.sub.3) δ 0.67 (s 3H), 0.70 (s, 3H), 0.90 (s, 3H), 0.93 (s, 3H), 1.21 (s, 3H), 1.34-1.75 (m, 8H), 1.50 (s, 3H), 1.53 (s, 3H), 1.56 (s, 3H), 1.88-2.25 (m, 12H), 1.99 (s, 3H), 2.02 (s, 3H), 2.25-2.46 (m, 1H), 2.73-2.90 (m, 1H), 3.20-3.70 (br m, 2H), 3.73 (br t, J=9.6 Hz, 1H), 4.00 (d, J=9.5 Hz, 1H), 4.01 (d, J=9.5 Hz, 1H), 4.90-5.10 (m, 4H), 5.23-5.39 (br s, 2H), 7.45-7.65 (m, 10H), 7.78-7.87 (m, 2H), 8.00-8.07 (m, 3H) ppm.

$^{13}$C NMR (75.45 MHz, CDCl$_3$) δ 9.1, 13.1, 13.4, 16.1, 16.4, 16.4, 16.4, 18.8, 18.8, 24.1, 24.1, 26.0, 26.0, 26.5, 27.5, 27.5, 29.7, 34.4, 35.5, 38.7, 38.7, 39.7, 39.7, 64.5, 73.6, 73.7, 75.7, 75.8, 116.9, 118.8, 127.8, 128.0, 128.1, 128.3, 128.4, 128.6, 128.6, 128.8, 132.6, 132.7, 133.3, 133.7, 133.7, 134.4, 137.8, 138.0, 139.2, 139.3, 139.4, 143.6, 143.6, 144.6 ppm.

IR (KBr) 3501, 2930, 1683, 1447, 1300, 1141, 1083, 756 cm$^{-1}$.

HRMS (FAB$^+$) m/z cacld for $C_{52}H_{71}O_5S_2(C_{58}H_{79}O_8S_3$—$C_6H_6SO_2$—$H_2O$) 839.4743, found 839.4730.

Example 11

2,7-Dibromo-1,9,18-tris(benzenesulfonyl)-3,7,12,16-tetramethyl-1,18-bis(2,-6,6-trimethyl-1-cyclohexen-1-yl)-3,7,11,15-octadecatetraene (P-1)

To a stirred solution of the $C_{40}$ diol compound (O) (0.13 g, 0.15 mmol) in $CH_2Cl_2$ (5 mL) at 0° C. were added pyridine

22

(0.054 mL, 0.60 mmol) and PBr$_3$ (0.011 mL, 0.12 mmol). The mixture was stirred at 0° C. for 40 min, diluted with $CH_2Cl_2$ (20 mL), washed with 1 M HCl solution (10 mL×3), dried over anhydrous $MgSO_4$, filtered, and concentrated under reduced pressure to give the di-bromination product (P-1) (0.17 g, 0.15 mmol) in 100% crude yield. This compound was not purified and directly utilized in the elimination reaction to produce β-carotene (see Example 15-A).

Example 12

1,9,18-Tris(benzenesulfonyl)-3,7,12,16-tetramethyl-1,18-bis(2,6,6-trimethyl-l-1-cyclohexen-1-yl)-3,7,11,15-octadecatetraene-2,17-diol, bis(tetrahydropyranyl)ether (P-2)

To a stirred solution of the $C_{40}$ diol compound (O) (0.55 g, 0.55 mmol) in $CH_2Cl_2$ (10 mL) were added 3,4-dihydro-2H-pyran (0.26 mL, 2.75 mmol) and 10-camphorsulfonic acid (80 mg, 0.33 mmol). The reaction mixture was stirred at room temperature for 15 h, diluted with $CH_2Cl_2$ (20 mL), washed with saturated $NaHCO_3$ solution (10 mL×2), dried over anhydrous $K_2CO_3$, filtered, and concentrated under reduced pressure. The crude product was purified by silica gel (deactivated by $Et_3N$) column chromatography to give the bis(tetrahydropyranyl)ether (P-2) (0.58 g, 0.49 mmol) in 90% yield.

$^1$H NMR (300.40 MHz, CDCl$_3$) δ 0.76 (s 3H), 0.78 (s, 3H), 1.05 (s, 3H), 1.08 (s, 3H), 1.20 (s, 3H), 1.30-2.25 (m, 47H), 2.25-2.47 (m, 1H), 2.73-2.92 (m, 1H), 3.28-3.28 (m, 2H), 3.58-3.92 (m, 2H), 3.92-4.25 (m, 3H), 4.38 (br s, 1H), 4.85 (br s, 1H), 4.97 (br s, 1H), 5.00 (br s, 1H), 5.10 (d, J=9.4 Hz, 1H), 5.12 (d, J=9.3 Hz, 1H), 5.30 (br s, 1H), 5.35 (br s, 1H), 7.43-7.65 (m, 10H), 7.77-7.87 (m, 2H), 7.98-8.15 (m, 3H) ppm.

IR (KBr) 2943, 1684, 1447, 1304, 1143, 1083, 1028 cm$^{-1}$.

Example 13

1,9,18-Tris(benzenesulfonyl)-3,7,12,16-tetramethyl-1,18-bis(2,6,6-trimethyl-1-cyclohexen-1-yl)-3,7,11,15-octadecatetraene-2,17-diol, bis(1-ethoxyethyl)ether (P-3)

To a stirred solution of the $C_{40}$ diol compound (O) (0.12 g, 0.13 mmol) in $CH_2Cl_2$ (5 mL) at 0° C. were added ethyl vinyl ether (0.71 mL, 0.73 mmol) and pyridinium p-toluenesulfonate (10 mg, 0.05 mmol). The mixture was stirred at room temperature for 20 h. The mixture was then diluted with $CH_2Cl_2$ (20 mL), washed with saturated $NaHCO_3$ (10 mL×3), dried over anhydrous $K_2CO_3$, filtered, and concentrated under reduced pressure. The crude product was purified by silica gel (deactivated by $Et_3N$) column chromatography to give the bis(1-ethoxyethyl)ether (P-3) (0.13 g, 0.12 mmol) in 90% yield.

$^1$H NMR (300.40 MHz, CDCl$_3$) δ 0.74 (t, J=6.1 Hz, 6H), 0.98-1.32 (m, 20H), 0.98-1.79 (m, 20H), 1.79-2.26 (m, 16H), 2.26-2.46 (m, 1H), 2.77-2.90 (m, 1H), 3.26 (dq, $J_d$=15.9, $J_q$=7.7 Hz, 1H), 3.44 (dq, $J_d$=15.5, $J_t$=7.8 Hz, 1H), 3.65-3.87 (m, 3H), 4.05 (d, J=10.3 Hz, 1H), 4.07 (d, J=9.9 Hz, 1H), 4.46-4.59 (m, 1H), 4.59-4.72 (m, 1H), 4.72-4.82 (m, 1H), 4.90-5.12 (m, 3H), 5.22-5.38 (m, 2H), 7.42-7.62 (m, 10H), 7.77-7.88 (m, 3H), 7.98-8.10 (m, 2H) ppm.

Example 14

1,9,18-Tris(benzenesulfonyl)-3,7,12,16-tetramethyl-1,18-bis(2,6,6-trimethyl-l-1-cyclohexen-1-yl)-3,7,11,15-octadecatetraene-2,17-diol, bis(methoxymethyl)ether (P-4)

To a stirred solution of the $C_{40}$ diol compound (O) (0.30 g, 0.30 mmol) in dimethoxy methane (1.1 mL, 12.12 mmol) at room temperature was added P$_2$O$_5$ (61 mg, 0.44 mmol). The resulting yellow solution was stirred for 12 h, and P$_2$O$_5$ (28 mg, 0.36 mmol) was added again. Stirring for another 4 h, the reaction mixture was diluted with toluene (30 mL), washed with saturated NaHCO$_3$ solution (10 mL×3), dried over anhydrous Na$_2$SO$_4$, filtered, and concentrated under reduced pressure. The crude product was purified by silica gel (deactivated by Et$_3$N) column chromatography to give the bis(methoxymethyl)ether (P-4) (0.31 g, 0.28 mmol) in 93% yield.

$^1$H NMR (300.40 MHz, CDCl$_3$) δ 0.73 (s, 3H), 0.75 (s, 3H), 0.84-2.27 (m, 20H), 1.11 (s, 3H), 1.13 (s, 3H), 1.18 (s, 3H), 1.41 (s, 3H), 1.44 (s, 3H), 1.56 (s, 3H), 2.05 (s, 3H), 2.08 (s, 3H), 2.27-2.47 (m, 1H), 2.60-2.94 (m, 1H), 3.44 (s, 3H), 3.64-3.78 (m, 1H), 4.05 (d, J=9.9 Hz, 1H), 4.07 (d, J=10.3 Hz, 1H), 4.50-4.72 (m, 4H), 4.72-5.10 (m, 4H), 5.32 (br s, 2H), 7.42-7.67 (m, 10H), 7.75-7.90 (m, 3H), 7.93-8.07 (m, 2H) ppm.

IR (KBr) 2931, 1446, 1301, 1141, 1083, 1021 cm$^{-1}$.

HRMS (FAB$^+$) m/z cacld for C$_{54}$H$_{75}$O$_6$S$_2$ (C$_{62}$H$_{87}$O$_{10}$S$_3$—C.sub.6H.sub.6SO.sub.2-CH$_3$OCH$_2$OH) 883.5005, found 883.4999.

Example 15

β-carotene (Chemical Formula 2)

Method A: Elimination Reaction from the Compound (P-1)

To a stirred suspension of the crude (see Example 11) C$_{40}$ dibromide (P-1) (0.15 g, 0.13 mmol) in cyclohexane (10 mL) and benzene (5 mL) was added KOMe (0.28 g, 3.99 mmol). The mixture was heated to 70~80° C. for 21 h, cooled to room temperature, and 1 M HCl (10 mL) was carefully added. The reaction mixture was extracted with a 9:1 (v:v) solution (30 mL) of hexane and benzene, dried over anhydrous Na$_2$SO$_4$, filtered, and concentrated under reduced pressure. The resulting red solid was diluted with hexane (30 mL) and washed with CH$_3$CN (10 mL×3). The combined CH$_3$CN solution was extracted again with hexanes. The hexane layers were combined and concentrated under reduced pressure to give β-carotene of the Chemical Formula 2 (56 mg, 0.10 mmol) in 77% crude yield. The crude product was purified by recrystallization from MeOH and THF to provide all-(E)-β-carotene (36 mg, 0.067 mmol) in 50% yield as a dark red crystal.

Method B: Elimination Reaction from the Compound (P-2)

To a stirred suspension of the bis(tetrahydropyranyl)ether (P-2) (0.55 g, 0.47 mmol) in cyclohexane (20 mL) and benzene (10 mL) was added KOMe (0.66 g, 9.40 mmol). The mixture was heated to 70~80° C. for 18 h, cooled to room temperature, and 1 M HCl (20 mL) was carefully added. The reaction mixture was extracted with a 9:1 (v:v) solution (40 mL) of hexane and benzene, dried over anhydrous Na$_2$SO$_4$, filtered, and concentrated under reduced pressure. The resulting red solid was diluted with hexane (30 mL) and washed with CH$_3$CN (10 mL×3). The combined CH$_3$CN solution was extracted again with hexanes. The hexane layers were combined and concentrated under reduced pressure to give .beta.-carotene of the Chemical Formula 2 (0.25 g, 0.47 mmol) in 100% crude yield. The crude product was purified by recrystallization from MeOH and THF to provide all-(E)-β-carotene (0.20 g, 0.38 mmol) in 81% yield as a dark red crystal.

Method C: Elimination Reaction from the Compound (P-3)

To a stirred suspension of the bis(1-ethoxyethyl)ether (P-3) (0.10 g, 0.09 mmol) in cyclohexane (10 mL) and benzene (5 mL) was added KOMe (0.18 g, 2.60 mmol). The mixture was heated to 70~80° C. for 17 h, cooled to room temperature, and 1 M HCl (5 mL) was carefully added. The reaction mixture was extracted with a 9:1 (v:v) solution (20 mL) of hexane and benzene, dried over anhydrous Na$_2$SO$_4$, filtered, and concentrated under reduced pressure. The resulting red solid was diluted with hexane (30 mL) and washed with CH$_3$CN (10 mL×3). The combined CH$_3$CN solution was extracted again with hexanes. The hexane layers were combined and concentrated under reduced pressure to give β-carotene of the Chemical Formula 2 (46 mg, 0.086 mmol) in 99% crude yield. The crude product was purified by recrystallization from MeOH and THF to provide all-(E)-β-carotene (32 mg, 0.059 mmol) in 70% yield as a dark red crystal.

Method D: Elimination Reaction from the Compound (P-4)

To a stirred solution of the bis(methoxymethyl)ether (P-4) (0.16 g, 0.14 mmol) in cyclohexane (10 mL) and benzene (5 mL) was added KOMe (0.19 g, 2.76 mmol). The mixture was heated to 70~80° C. for 18 h, cooled to room temperature, and 1 M HCl (10 mL) was carefully added. The reaction mixture was extracted with a 9:1 (v:v) solution (30 mL) of hexane and benzene, dried over anhydrous Na$_2$SO$_4$, filtered, and concentrated under reduced pressure. The resulting red solid was diluted with hexane (30 mL) and washed with CH$_3$CN (10 mL×3). The combined CH$_3$CN solution was extracted again with hexanes. The hexane layers were combined and concentrated under reduced pressure to give β-carotene of the Chemical Formula 2 (67 mg, 0.13 mmol) in 91% crude yield. The crude product was purified by recrystallization from MeOH and THF to provide all-(E)-β-carotene (53 mg, 0.10 mmol) in 71% yield as a dark red crystal.

The $^1$H NMR spectra of all-(E)-β-carotene, which were prepared according to the above methods A-D, were identical to that of the authentic sample.

Industrial Applicability

The novel C$_{20}$ dialdehyde compound of the Chemical Formula 3 according to the present invention can be expeditiously prepared from the readily available geraniol, and can be efficiently utilized in the syntheses of the conjugated polyene chains of the carotenoid compounds such as lycopene and β-carotene by the sulfone-mediated coupling and double elimination reactions. The processes of the coupling reaction between the above C$_{20}$ dialdehyde and two equivalents of geranyl sulfone or cyclic geranyl sulfone, the protection of the resulting C$_{40}$ diols, and then the double elimination reactions of the protected C$_{40}$ compounds are highly efficient in producing lycopene and β-carotene in much shorter steps with great economical values than the previous sulfone-mediated methods.

Therefore, the syntheses of lycopene and β-carotene according to the present invention have several advantages over the existing methods especially in the fast preparation of the starting materials for the coupling reaction, the efficiency of the reaction steps, and the easy handling of the intermediates, by-product, and the product, not to mention of the formation of (E)-configuration in the carbon-carbon double bonds.

The invention claimed is:

1. A process for preparing lycopene of the Chemical Formula 1, which comprises the steps of:
   (a-2) deprotonating geranyl sulfone (I), and then reacting with the C$_{20}$ dialdehyde of the Chemical Formula 3 to synthesize the C$_{40}$ diol compound (L);

(b-2) applying functional group transformation reactions to the above $C_{40}$ diol compound (L) to produce the corresponding dihalide or diether compound (M); and finally (c-2) reacting the above protected diol compound (M) with a base to induce the double elimination reactions of the sulfone and the halogen or the ether functional groups, thereby producing the conjugated polyene chain,

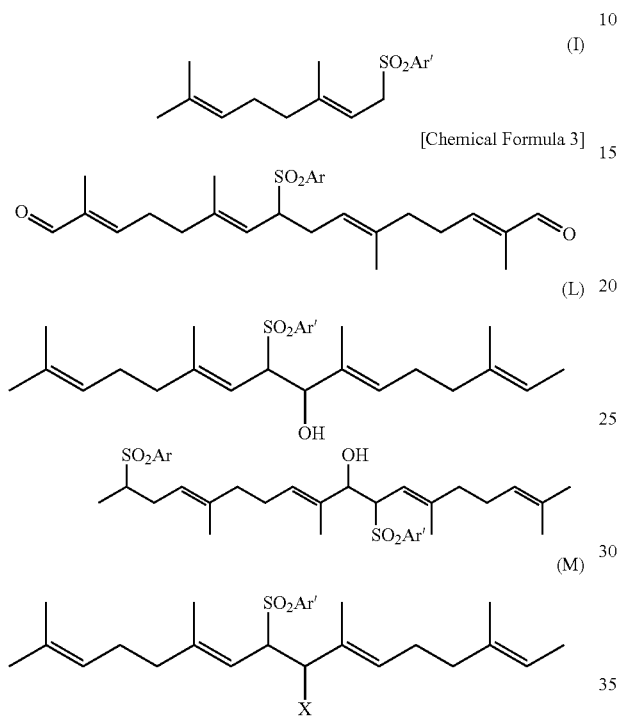

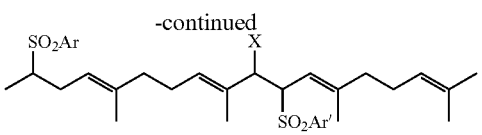

[Chemical Formula 1]

wherein, in the formulas, Ar and Ar' independently represent the groups of $C_6$-$C_{30}$ substituted or unsubstituted aryl, or $C_2$-$C_{20}$ substituted or unsubstituted heteroaryl;

X represents the groups of halogen atom or $C_1$-$C_{20}$ substituted or unsubstituted alkoxy.

2. A process for preparing lycopene of the Chemical Formula 1 according to claim 1, wherein the functional group transformation reactions of the $C_{40}$ diol compound (L) in step (b-2) are carried out by reacting with $(COCl)_2$, $SOCl_2$ or $PBr_3$ to produce the corresponding the dihalide compound (M), or by reacting with 3,4-dihydro-2H-pyran or ethyl vinyl ether in the presence of p-toluenesulfonic acid or 10-camphorsulfonic acid catalyst, or by reacting with dimethoxymethane in the presence of $P_2O_5$ to produce the corresponding ether compound (M).

* * * * *